US00PP16071P2

(12) United States Plant Patent
McLaren

(10) Patent No.: US PP16,071 P2
(45) Date of Patent: Oct. 25, 2005

(54) APRICOT TREE, 'F168 CV'

(50) Latin Name: *Prunus armeniaca* L
Varietal Denomination: F168 cv

(75) Inventor: John McLaren, Cromwell (NZ)

(73) Assignee: Nevis Fruit Company USA LLC, Boulder, CO (US)

( * ) Notice: Subject to any disclaimer, the term of this patent is extended or adjusted under 35 U.S.C. 154(b) by 86 days.

(21) Appl. No.: 10/846,092

(22) Filed: May 14, 2004

(51) Int. Cl.[7] ..... A01H 5/00
(52) U.S. Cl. ..... Plt./186
(58) Field of Search ..... Plt./186

*Primary Examiner*—Anne Marie Grunberg
(74) *Attorney, Agent, or Firm*—Wells St. John P.S.

(57) ABSTRACT

A new and distinct variety of apricot tree is disclosed and which is mature for harvesting and shipment under the ecological conditions prevailing in Eastern Washington about August 29$^{th}$.

3 Drawing Sheets

BACKGROUND OF THE NEW VARIETY

The present invention relates to a new and distinct variety of apricot tree, (*Prunus armeniaca* L.) and which has been denominated varietally as 'F168 cv' hereinafter, and more specifically to a new apricot tree variety which is characterized as to novelty by bearing medium sized attractively colored fruit which are ripe for harvesting and shipment about six weeks later than the harvesting dates for more common apricot varieties such as "Perfection" and "Moorpark" both of which are unpatented when grown under the ecological conditions prevailing in Eastern Washington.

ASEXUAL REPRODUCTION

The present variety of apricot tree was originated by me from a cross which I conducted in 1987 between the unpatented apricot varieties "Sundrop" (female parent) with a late "Moorpark (male parent)." I conducted this cross at my orchard which is located in Central Otago, New Zealand. The present variety showed noteworthy characteristics and was selected for further evaluation. In 1995, budwood of the present variety was sent to the quarantine facility, IR-2, at Prosser, Wash. for further virus testing. Subsequently, virus-free material was released from the same facility in 1999, and test trees were grafted and subsequently planted in a test orchard which is located near Orondo, Wash. Still further, 30 third generation trees were planted in the same test orchard in Orondo, Wash. in 2002. The original test trees planted in 1999, and the subsequent third generation trees have been continually observed and the fruit thereof have been compared and contrasted with that of the original tree. It has been determined that the characteristics of the present tree are true to the original selection.

SUMMARY OF THE VARIETY

The new variety of apricot tree, 'F168 cv' is characterized as to novelty, and is otherwise deemed noteworthy by producing fruit which ripen for commercial harvesting and shipment about August 29$^{th}$ under the ecological conditions prevailing in Orondo, Wash. Still further, the present variety produces a semi-clingstone fruit having a firm, crisp flesh texture at commercial maturity.

BRIEF DESCRIPTION OF THE DRAWINGS

The accompanying drawings are color photographs of various aspects of the present plant. The colors are as nearly true as is reasonably possible in color representations of this type. Due to chemical development, processing and printing, the leaves and fruit of the present tree may, or may not be, accurate when compared to the actual specimen. For this reason, future color references should be made to the color plates as provided by the Munsell Book of Color, and the other general color descriptions as provided for hereinafter.

DETAILED DESCRIPTION

Figure 1:
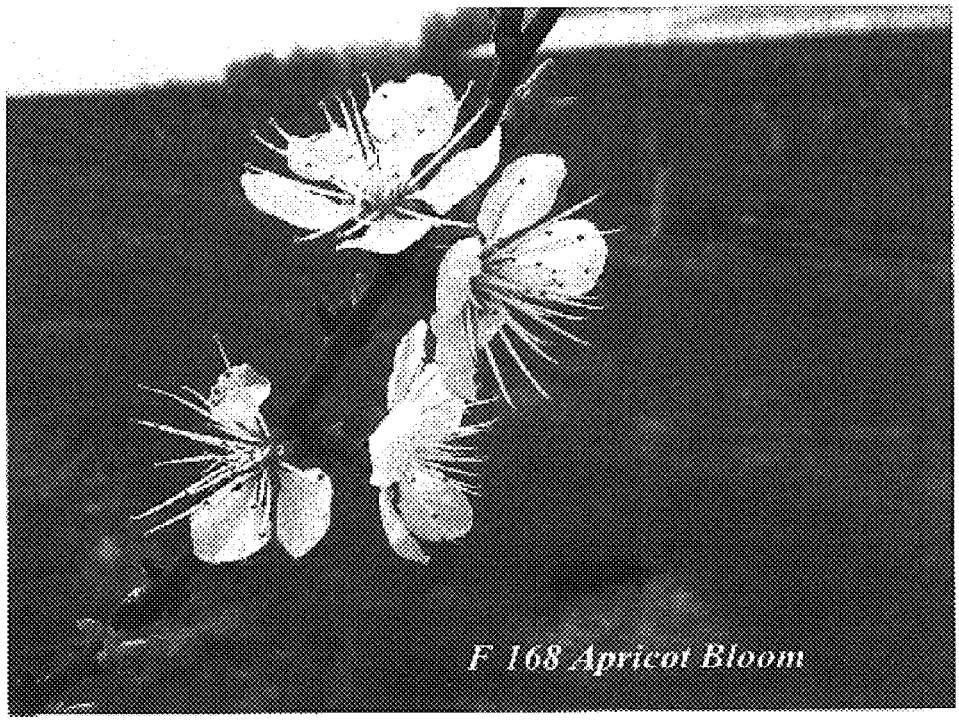
FIG. 1 depicts the bloom characteristics of the present variety of apricot tree as seen on Apr. 3, 2003 at the test orchard referenced above.
Figure 2:
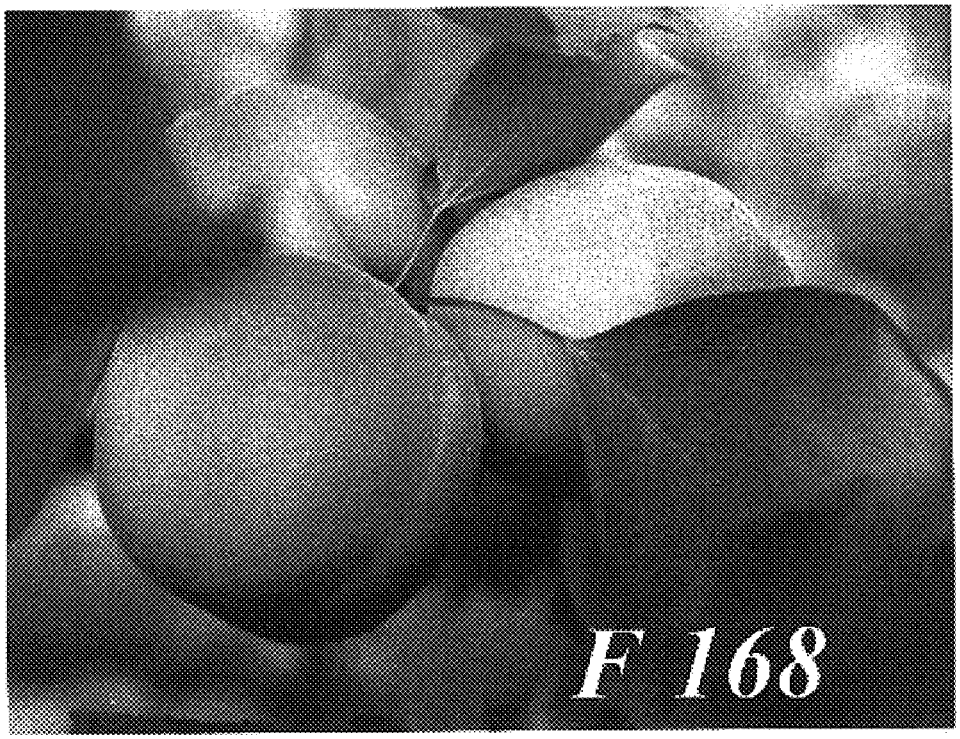
FIG. 2 illustrates the fruit of the present variety of apricot tree at a stage of development where it is sufficiently matured for harvesting and shipment.
Figure 3:
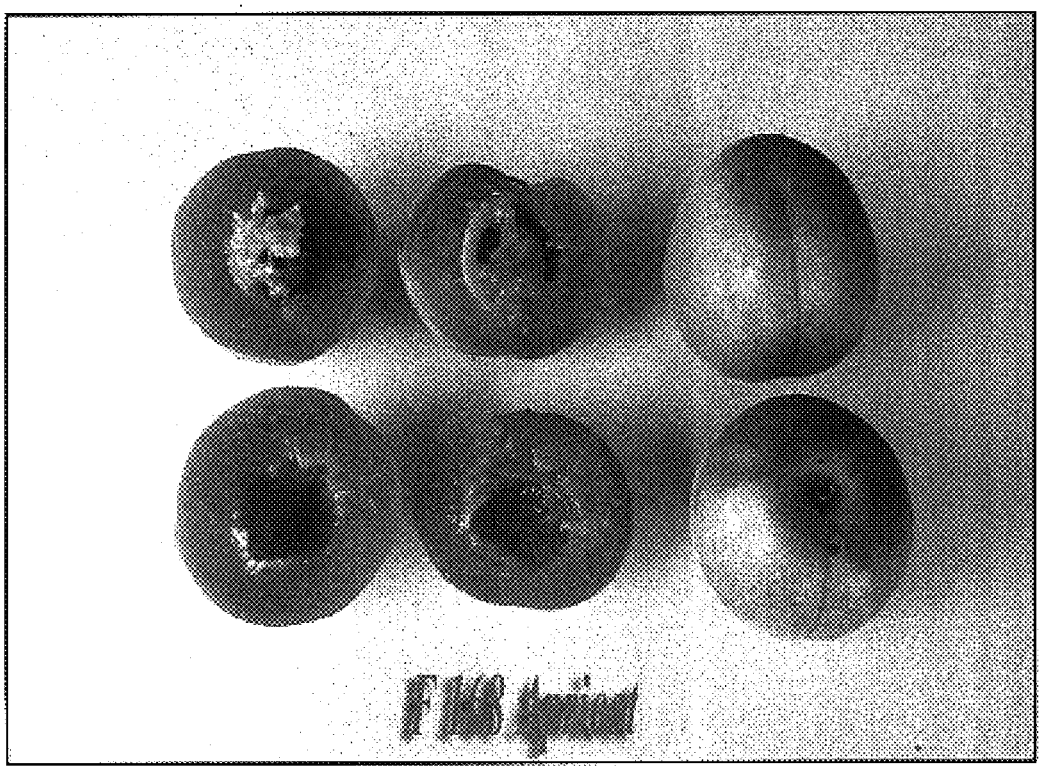
FIG. 3 illustrates several mature fruit of the present variety and several other fruit which have been dissected in the longitudinal and transverse planes, and which shows the flesh and stone characteristics thereof.
Figure 4:
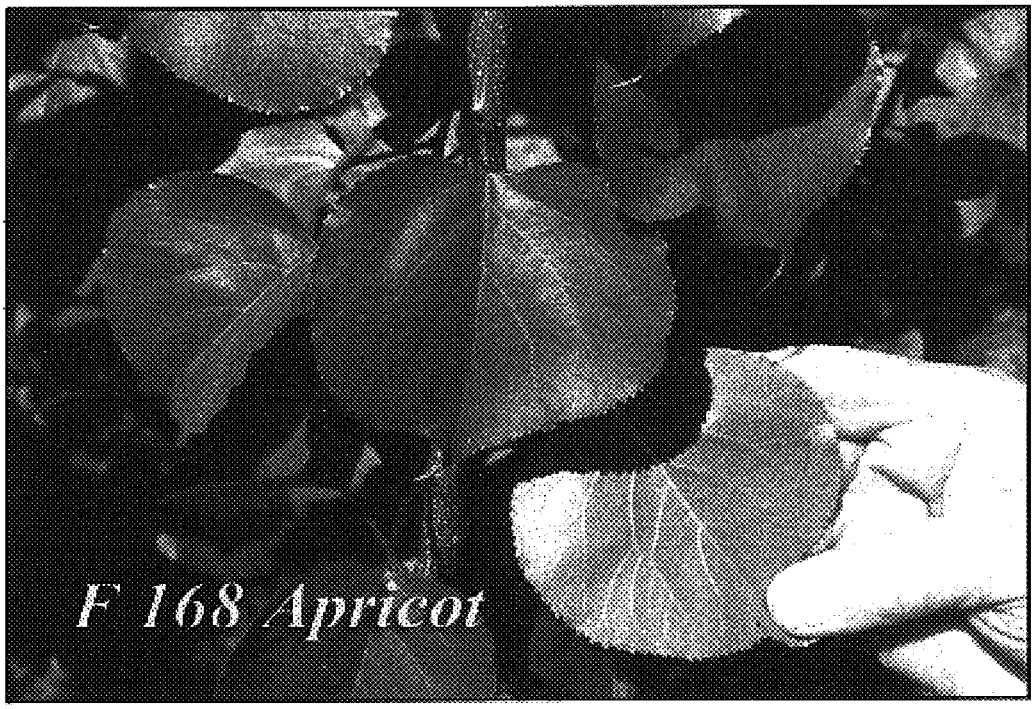
FIG. 4 shows the dorsal and ventral surfaces of mature leaves of the new apricot tree variety.
Figure 5:
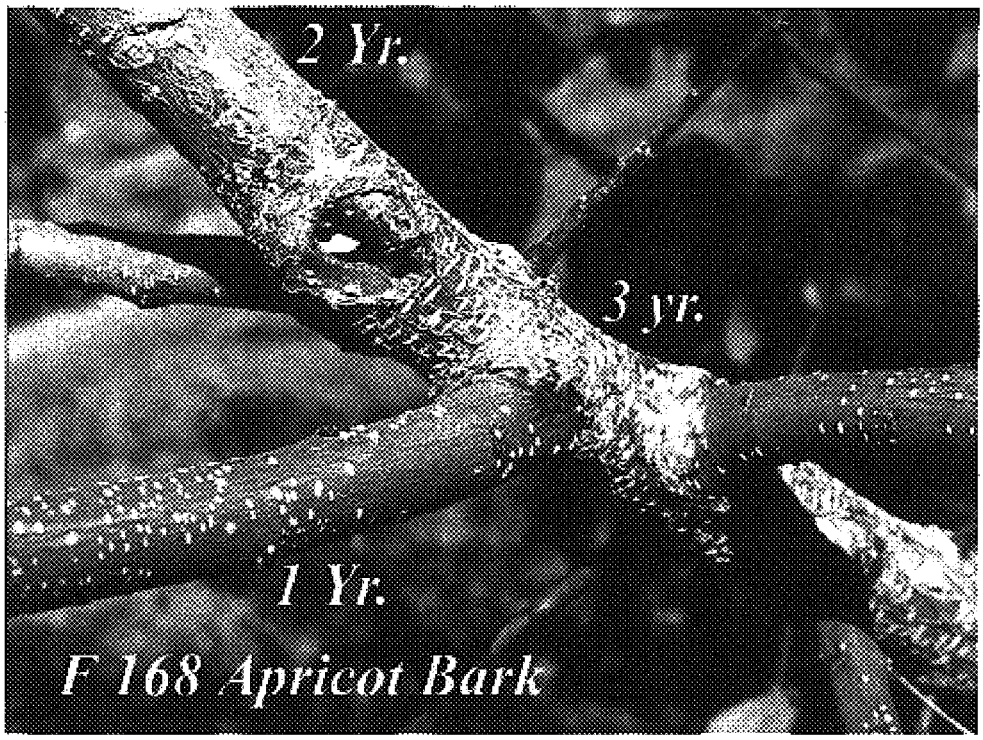
FIG. 5 illustrates the characteristics of both first, second and third year wood currently growing on a test tree.
Figure 6:
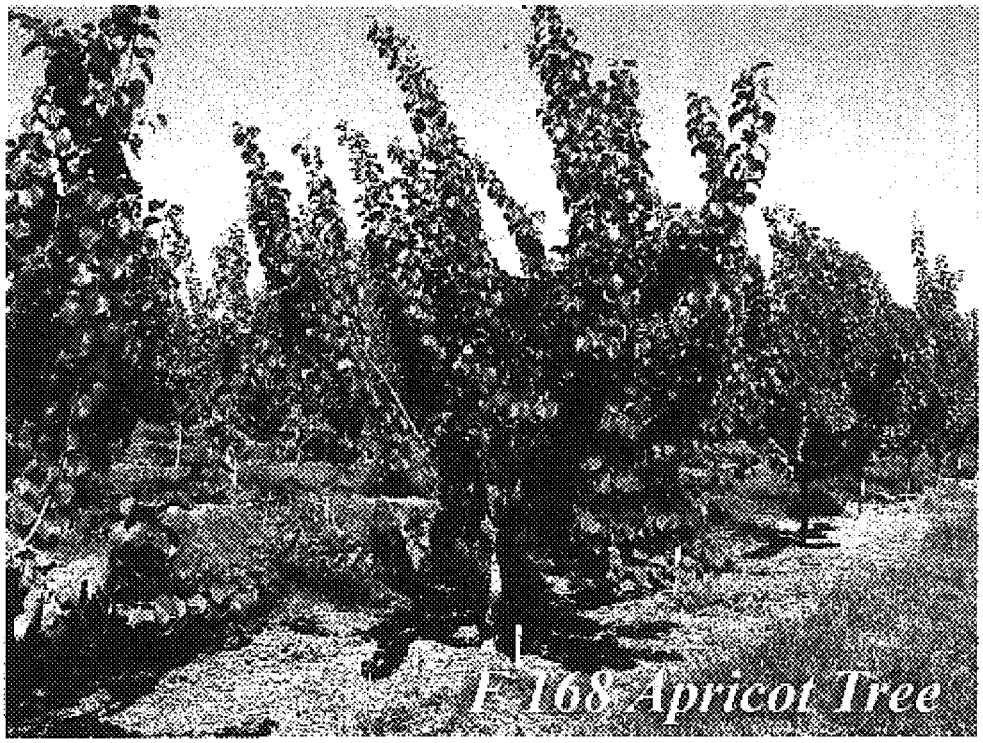
FIG. 6 shows the growing habit of a test tree as presently growing during the 2003 growing season.

Referring more specifically to the pomological details of this new and distinct variety of apricot tree, the following has been observed during the 2003 growing season under the ecological conditions prevailing in a test orchard which is located near Orondo, Wash. All major color code designations are by reference to the Munsell book of Color. Common color names are also used occasionally.

TREE

Tree size: Considered average. Fifth leaf trees (five years in the field) have a height of about 3 meters; and a width of about 3 meters.

Productivity: Considered moderate. This characteristic is not particularly distinctive of the present variety, however.

Vigor: Considered vigorous. The present variety shows about 1 to about 1.5 meters of annual growth. All test trees grown at the experimental orchard, which is located at Orondo, Wash., were grafted onto "Manchurian" (unpatented) apricot rootstock.

Growing habit: Considered spreading.

Chilling requirement: The chilling requirement of the present variety appears to be similar to other common commercial apricot varieties, based upon the observations of these trees as grown in the state of Washington. Actual chilling requirements of the subject tree have not been determined, however.

Regularity of bearing: Regular and uniform.

TRUNK

Size: Considered average for this variety. The present tree was about 5 cm. in diameter when measured at a distance of about 0.3 meters from the surface of the ground. This measurement was taken on third-leaf trees.

Bark color: Yellow-brown on 3 year old wood (7.5 YR 5/10).

Bark lenticels:
*Color.*—Light tan (7.5 YR 7/4).

Bark lenticels:
*Size.*—About 5 mm. long, and about 1 mm. wide.

Bark lenticels:
*Density.*—Typically 2 per square cm.

BRANCHES

Growth habit: Generally considered typical of most apricot trees, that is, spreading, and normally having new, vigorous, vertically oriented shoots.

Bark color:
*New growth.*—Green (2.5 GY 4/6) and later becoming a shade of purple (7.5 R 3/6) with increasing senescence. Bark color at full maturity is brown (7.5 YR 4/4).

Pubescence: Glabrous.

Bark lenticels:
*Numbers.*—Numerous, typically 8 to about 10 lenticels are observed per square cm.

Bark lenticels:
*Shape.*—Considered round to oblong, and having a dimension of about 1 to about 5 mm.

Lenticels:
*Color.*—Tan (10 YR 7/4).

Internodes:
*Length.*—Considered average and about 1.5 to about 2 cm. when measured on vigorous, current season shoots.

LEAVES

Leaf size:
*Generally.*—Considered average. Mature leaves have a length dimension of about 7.8 cm.; and a width dimension of about 7.2 cm.

Leaf form: Generally considered to be a typical arpicot leaf. In this regard, the leaf appears somewhat rounded, and having an acuminate tip.

Leaf margin:
*Form.*—Finely to coarsely crenate. Approximately 5 crenations are found per cm.

Leaf color:
*Dorsal surface.*—Dark green (5 GY 4/4).

Leaf color:
*Ventral surface.*—Light green (5 GY 6/4).

Leaf color:
*Mid vein.*—Green (2.5 GY 7/6).

Leaf glandular characteristics: Typically 4 to about 7 round glands appear on the dorsal facing surface.

Leaf petiole:
*Size.*—Considered average for the variety, and having a length dimension of about 22 mm.; and a thickness dimension of about 1.5 mm.

Leaf petiole:
*Color.*—Variable, and having a red color (7.5 R 2.8) on the dorsal surface; and a ventral color which varies from red to green (7.5 R 2/8 to 2.5 GY 6/4).

Mid-vein thickness: Average, about 1.5 mm.

Leaf blade:
*Shape.*—Appears typical for an apricot tree, that is, having an acuminate tip, and a base which may be acute to straight. About 8 coarsely crenate serrations appear per cm.

FLOWER

Fertility: It is unknown whether the variety is self-compatible.

Time of bloom: Date of full bloom was observed on Mar. 23, 2003 under the prevailing ecological conditions existing near Orondo, Wash. First Bloom was observed on Mar. 19, 2003. Petal fall was observed on Mar. 31, 2003.

Flower buds:
*Size.*—Dormant flower buds have a length dimension of about 3.5 mm.; and a width dimension of about 1.5 mm.

Flower buds:
*Surface texture.*—Glabrous.

Flower buds:
*Color.*—At the dormant stage, the flower buds are brown (2.5 YR 2/4).

Size of flower: On average, about 4.5 cm. in diameter at full bloom.

Flower petals:
*Length.*—About 20 mm.

Flower petals:
*Width.*—About 14 mm.

Flower petals:
*Color.*—White when fully open; and light pink (2.5 R 9/2) at the popcorn stage.

Sepals:
*Color.*—Bright red (5 R 4/14).

Stamens:
*Number.*—About 23 are found per flower.

Stamens:
*Length.*—About 18 mm.

Anthers:
*Color.*—Yellow (2.5 Y 8.14).

Anthers:
*Shape.*—Considered round and oblong.

Pistil:
*Length.*—About 15 mm.

Stigma:
*Length.*—About 1 mm.

FRUIT

Maturity when described: Generally, the fruit produced by the present variety of apricot tree is described as it will be found at full commercial maturity. In this regard, the fruit of the present variety was ripe for commercial harvesting and shipment under the ecological conditions prevailing near Orondo, Wash. on Aug. 29, 2003. This harvesting date is at least six weeks later than other common mid-season varieties such as "Perfection", and "Moorpark" both of which are unpatented, at the same geographical location.

Fruit size: Considered medium for the species. The average weight of the harvested fruit was about 60 grams.

Fruit form: Generally glabrous and having a diameter of about 45 mm.

Stem attachment:

*Generally.*—Considered strong. The stem commonly remains with the fruit rather than pulling out as is typically the situation for most apricot varieties. It was observed that the flesh of the present variety of apricot tree does not tear when it's picked.

Stem cavity:

*Size.*—About 3 mm. deep; and about 15 mm. wide.

Suture:

*Shape.*—Shallow and typically having a depth of less than about 1 mm.

Skin thickness: Considered thin, tender and crisp.

Skin texture: Smooth, and having a fine pubescence.

Blush color: Light red (7.5 R 5/12). The blush appears on about 25% of the fruit harvested.

Ground color: Light orange (7.5 YR 8/10 ). Some greenish overtones appear on fruit that is not completely ripe.

Tendency to crack: Not observed.

Flesh color: Considered bright orange (5 YR 7/14).

Juice production: Considered very juicy.

Flesh flavor: Considered sweet, and mildly acidic.

Soluble solids: About 18% at full commercial maturity.

Aroma: Typical for the species.

Flesh texture: Relatively firm and somewhat crisp at full commercial maturity.

Fibers: Not observed.

Ripening characteristics: Uniform and considered quite firm at full commercial maturity.

Eating quality: Considered excellent.

STONE

Attachment: Generally considered to be a semi-clingstone. Some flesh clings to the pit even at full commercial maturity.

Fibers: Not observed.

Stone size:

*Length.*—About 30 mm.

Stone size:

*Width.*—About 21 mm.

Stone thickness: About 13 mm.

Stone form: Ovoid.

Stone:

*Base.*—Rounded.

Apex shape: Blunt and rounded.

Stone side-shape: Considered equal.

Stone ridges: Typically, three ridges appear. They are medium in size and have a sharp texture.

Stone surface texture: Average, considered smooth and somewhat dull in appearance.

Stone color: When the stone is dry it has a dark brown color (5 YR 4/4).

Pit color: Light tan (7.5 YR 7/6).

Pit:

*Flavor.*—The pit has a bitter almond flavor. The pits have a hard shell.

Intended use: The present variety appears to be useful for the commercial, fresh market.

Disease and insect resistance: No susceptibilities were noted.

Keeping quality: Considered excellent. The fruit of the present variety of apricot tree has been kept up to 4 weeks in cold storage at a temperature of 33 degrees F.

Although the new variety of apricot tree possesses the described characteristics as a result of the growing conditions prevailing in Eastern Washington, it is to be understood that variations in the usual magnitude and characteristics incident to growing conditions, fertilization, pruning and pest control are to be expected.

Having thus described and illustrated my new variety of apricot tree, what I claim is new and desire to secure by Plant Letters Patent is:

1. A new and distinct variety of apricot tree substantially as illustrated and described, and which produces fruit which are mature for harvesting and shipment about August $29^{th}$ under the ecological conditions prevailing in Eastern Washington and which further has an attractive skin coloration, and which produces a firm, semi-free stone fruit at full commercial maturity.

* * * * *